United States Patent
Tasz et al.

(10) Patent No.: US 9,040,024 B2
(45) Date of Patent: *May 26, 2015

(54) COMPOSITION AND AEROSOL SPRAY DISPENSER FOR ELIMINATING ODORS IN AIR

(71) Applicant: S.C. Johnson & Son, Inc., Racine, WI (US)

(72) Inventors: Maciej K. Tasz, Racine, WI (US); Richard S. Valpey, III, Rockaway, NJ (US); Paul A. Clark, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/784,981

(22) Filed: Mar. 5, 2013

(65) Prior Publication Data

US 2013/0181013 A1  Jul. 18, 2013

Related U.S. Application Data

(60) Division of application No. 11/681,043, filed on Mar. 1, 2007, now Pat. No. 8,465,728, which is a continuation-in-part of application No. 11/476,243, filed on Jun. 28, 2006, now Pat. No. 8,440,171.

(60) Provisional application No. 60/694,439, filed on Jun. 28, 2005.

(51) Int. Cl.
*A61L 9/14* (2006.01)
*A61L 9/01* (2006.01)
(Continued)

(52) U.S. Cl.
CPC ... *A61L 9/14* (2013.01); *A61L 9/01* (2013.01); *A61L 9/145* (2013.01); *A61L 2209/134* (2013.01); *A61L 2209/22* (2013.01); *B65D 83/48* (2013.01)

(58) Field of Classification Search
None
See application file for complete search history.

(56) References Cited

U.S. PATENT DOCUMENTS

| | | |
|---|---|---|
| 2,757,278 A | 7/1956 | Cloud |
| 2,964,165 A | 12/1960 | Riley |

(Continued)

FOREIGN PATENT DOCUMENTS

| | | |
|---|---|---|
| EP | 0420538 A1 | 4/1991 |
| EP | 0510352 A2 | 10/1992 |

(Continued)

OTHER PUBLICATIONS

The Merck Index, 10th Edition, Merck & Co., Inc.: Rahway, NJ, 1983, pp. 10 (acetone: entry 58), pp. 34-35 (alcohol, anhydrous: entry 212), and pp. 749 (isopropyl alcohol: entry 5057).

(Continued)

*Primary Examiner* — Abigail Fisher
*Assistant Examiner* — Daniel L Branson

(57) ABSTRACT

An air treating composition for eliminating airborne malodors and/or sanitizing air in combination with a spray valve and actuator and spray performance parameters providing maximum dispersion of the composition is disclosed. The particles of the composition are small so that the active component is dispersed into air as a fine dispersion to provide more contact with malodors and to provide quick absorption of malodors and/or bacteria. The particle size of the composition is controlled through the valve and actuator dimensions, as well as the formulation requirements of the composition. The air treating composition includes water, a low molecular weight polyol, and a propellant. The composition may also include one or more adjuvants such as an emulsifier, a co-solvent, a fragrance, a corrosion inhibitor, a pH adjusting agent and the like.

6 Claims, 3 Drawing Sheets

(51) Int. Cl.
  *B65D 83/48* (2006.01)
  *B65D 83/14* (2006.01)

(56) References Cited

U.S. PATENT DOCUMENTS

| | | | |
|---|---|---|---|
| 3,131,153 | A | 4/1964 | Klausner |
| 3,160,555 | A | 12/1964 | Hamill et al. |
| 3,787,566 | A | 1/1974 | Gauvreau |
| 3,821,413 | A | 6/1974 | Hellyer, Jr. |
| 3,854,636 | A | 12/1974 | Conway et al. |
| 4,250,165 | A | 2/1981 | Foley |
| 4,294,821 | A | 10/1981 | Neumiller |
| 4,350,605 | A | 9/1982 | Hughett |
| 4,427,366 | A | 1/1984 | Moore |
| 4,469,848 | A | 9/1984 | Hooper et al. |
| 4,670,171 | A | 6/1987 | Magyar |
| 4,748,279 | A | 5/1988 | Whiteley |
| 4,797,420 | A | 1/1989 | Bryant |
| 4,938,416 | A | 7/1990 | Bertrand et al. |
| 4,940,170 | A | 7/1990 | Popp-Ginsbach |
| 4,940,171 | A | 7/1990 | Gilroy |
| 5,091,111 | A | 2/1992 | Neumiller |
| 5,125,546 | A | 6/1992 | Dunne et al. |
| 5,135,747 | A | 8/1992 | Faryniarz et al. |
| 5,143,288 | A | 9/1992 | Kohler et al. |
| 5,211,317 | A | 5/1993 | Diamond et al. |
| 5,297,566 | A | 3/1994 | Firstenberg et al. |
| 5,356,479 | A | 10/1994 | Menke et al. |
| 5,534,249 | A | 7/1996 | Maurer |
| 5,578,563 | A | 11/1996 | Trinh et al. |
| 5,586,695 | A | 12/1996 | Labus et al. |
| 5,591,395 | A | 1/1997 | Schroeder et al. |
| 5,663,134 | A | 9/1997 | Trinh et al. |
| 5,670,475 | A | 9/1997 | Trinh et al. |
| 5,702,631 | A | 12/1997 | Conville et al. |
| 5,773,016 | A | 6/1998 | Nelson |
| RE35,843 | E | 7/1998 | Diamond et al. |
| 5,782,409 | A | 7/1998 | Paul |
| 5,783,544 | A | 7/1998 | Trinh et al. |
| 5,891,426 | A | 4/1999 | Jarrousse et al. |
| 5,905,066 | A | 5/1999 | Zocchi et al. |
| 5,906,992 | A | 5/1999 | Fonsny et al. |
| 5,939,060 | A | 8/1999 | Trinh et al. |
| 5,942,482 | A | 8/1999 | Zocchi et al. |
| 5,955,093 | A | 9/1999 | Woo et al. |
| 5,985,814 | A | 11/1999 | Zocchi et al. |
| 5,990,157 | A | 11/1999 | Zocchi et al. |
| 6,077,318 | A | 6/2000 | Trinh et al. |
| 6,080,792 | A | 6/2000 | Zocchi et al. |
| 6,087,402 | A | 7/2000 | Zocchi et al. |
| 6,127,416 | A | 10/2000 | Fonsny et al. |
| 6,146,621 | A | 11/2000 | Trinh et al. |
| 6,173,907 | B1 | 1/2001 | Benoist |
| 6,231,837 | B1 | 5/2001 | Stroud et al. |
| 6,248,135 | B1 | 6/2001 | Trinh et al. |
| 6,284,231 | B1 | 9/2001 | Trinh et al. |
| 6,302,969 | B2 | 10/2001 | Moster et al. |
| 6,395,236 | B1 | 5/2002 | Stewart |
| 6,451,065 | B2 | 9/2002 | Trinh et al. |
| 6,569,387 | B1 | 5/2003 | Furner et al. |
| 6,592,813 | B1 | 7/2003 | Fox et al. |
| 6,610,254 | B1 | 8/2003 | Furner et al. |
| 6,701,922 | B2 | 3/2004 | Hindle et al. |
| 6,824,079 | B2 | 11/2004 | Kendrick et al. |
| 6,987,099 | B2 | 1/2006 | Trinh et al. |
| 7,014,127 | B2 | 3/2006 | Valpey, III et al. |
| 7,307,053 | B2 | 12/2007 | Tasz et al. |
| 2001/0011687 | A1 | 8/2001 | Benoist |
| 2002/0002123 | A1 | 1/2002 | McGee et al. |
| 2003/0071080 | A1 | 4/2003 | Yquel |
| 2003/0138465 | A9 | 7/2003 | Douin et al. |
| 2003/0145965 | A1 | 8/2003 | Anderson et al. |
| 2003/0150885 | A1 | 8/2003 | Dunne |
| 2003/0213818 | A1 | 11/2003 | Hilvert et al. |
| 2004/0026462 | A1 | 2/2004 | Moshontz et al. |
| 2004/0082473 | A1 | 4/2004 | Beilfuss et al. |
| 2004/0101459 | A1 | 5/2004 | Schur |
| 2004/0144864 | A1 | 7/2004 | Valpey, III et al. |
| 2004/0223871 | A1 | 11/2004 | Woo et al. |
| 2004/0223943 | A1 | 11/2004 | Woo et al. |
| 2005/0003990 | A1 | 1/2005 | Smith et al. |
| 2005/0023368 | A1 | 2/2005 | Valpey et al. |
| 2005/0026796 | A1 | 2/2005 | Leonard et al. |
| 2005/0031498 | A1 | 2/2005 | Held |
| 2005/0098588 | A1 | 5/2005 | Dunne |
| 2005/0124512 | A1 | 6/2005 | Woo et al. |
| 2006/0026817 | A1 | 2/2006 | Valpey, III et al. |
| 2006/0051384 | A1 | 3/2006 | Scholz et al. |
| 2006/0057521 | A1 | 3/2006 | Kubicek et al. |
| 2006/0228250 | A1 | 10/2006 | Brown et al. |
| 2006/0263236 | A1 | 11/2006 | Woo et al. |
| 2006/0292111 | A1 | 12/2006 | Valpey, III et al. |
| 2007/0122373 | A1 | 5/2007 | Woo et al. |
| 2007/0172382 | A1 | 7/2007 | Uchiyama et al. |
| 2007/0194040 | A1 | 8/2007 | Tasz et al. |
| 2008/0003185 | A1 | 1/2008 | Valpey, III et al. |
| 2008/0111005 | A1 | 5/2008 | Campbell et al. |
| 2011/0318222 | A1 | 12/2011 | Uchiyama et al. |

FOREIGN PATENT DOCUMENTS

| | | |
|---|---|---|
| EP | 1760139 A1 | 3/2007 |
| GB | 19603 | 0/1896 |
| GB | 998776 | 7/1965 |
| GB | 999837 | 7/1965 |
| GB | 1498935 | 1/1978 |
| JP | 57-159707 | 10/1982 |
| JP | 2001-72152 A | 3/2001 |
| JP | 2003-012422 A | 1/2003 |
| JP | 2006-022292 A | 1/2006 |
| WO | 00/54585 A1 | 9/2000 |
| WO | 03/099976 A1 | 12/2003 |
| WO | 2004/026462 A1 | 4/2004 |
| WO | 2004/067406 A1 | 8/2004 |
| WO | 2006/102052 A2 | 9/2006 |
| WO | 2007/002778 A1 | 1/2007 |

OTHER PUBLICATIONS

The Merck Index, 10th Edition, Merck & Co., Inc.: Rahway, NJ, 1983, pp. 51 (entry 338), pp. 453 (entry 3104), pp. 550 (entry 3744), pp. 1130-1131 (entry 7756), and pp. 1382 (entry 9480).

"HLB Systems", accessed on Jun. 11, 2011 at pharmcal.tripod.com/ch17.htm.

Brown et al, Chemistry: The Central Science, 6th Edition, Prentice Hall, Englewood Cliffs, NJ, 1994, pp. 1016 (Table D.1).

Pesticides: Science and Policy, DIS/TSS-11, Efficacy Data and Labeling Requirements: Air Sanitizers; Sep. 3, 1980, pp. 1-4.

The Encyclopedia of Chemistry, 3rd Edition, Clifford A. Hampel and Gessner G. Hawley, eds., Van Nostrand Reinhold Company: New York, 1973, pp. 38-39.

COMPOSITION AND AEROSOL SPRAY DISPENSER FOR ELIMINATING ODORS IN AIR

CROSS REFERENCE TO RELATED APPLICATION

This application is a division of U.S. patent application Ser. No. 11/681,043, filed on Mar. 1, 2007, which in turn is a continuation-in-part out of U.S. patent application Ser. No. 11/476,243, filed on Jun. 28, 2006, which is related to, and claims the priority benefit of, U.S. Provisional Patent Application No. 60/694,439, filed Jun. 28, 2005.

BACKGROUND

1. Technical Field

This disclosure is directed to a deodorant and air sanitizing aerosol spray composition in combination with a spray valve and spray performance parameters to provide optimum dispersion of the composition into the surrounding air.

2. Description of the Related Art

Various compositions are available to mask malodors in the air. Additionally, various compositions are available to sanitize and remove malodors from the air. These compositions may be dispensed by various spray devices including aerosol dispensers.

Aerosol dispensers have been commonly used to dispense personal, household, industrial, and medical products, and to provide a low cost, easy to use method of dispensing a liquid product. Typically, aerosol dispensers include a container, which contains a liquid product to be dispensed. A propellant is used to discharge the liquid from the container. The propellant, which may be a mixture, typically has a boiling point slightly below room temperature so that, under pressure, the propellant exists as equilibrium between a vapor phase and a liquid phase. The vapor phase of the propellant provides sufficient force to expel the liquid product from the container when a user actuates a discharge valve by, for example, pressing an actuator button. When the valve is closed and the container is resealed, the vapor phase of the propellant is replenished by the liquid phase as the equilibrium between the vapor and liquid phases is reestablished within the container.

As illustrated in FIG. 3, a conventional aerosol dispenser generally comprises a container (not shown) for holding a liquid product and a propellant, and a valve assembly 104 for selectively dispensing a liquid product from the container. The valve assembly 104 comprises a mounting cup 106, a mounting gasket 108, a valve body 110, a valve stem 112, a stem gasket 114, an actuator cap 116, and a return spring 118. The valve stem 112, stem gasket 114, and return spring 118 are disposed within the valve body 110 and are movable relative to the valve body 110 to selectively control dispensing of the liquid product. The valve body 110 is affixed to the underside of the mounting cup 106, such that the valve stem 112 extends through, and projects outwardly from, the mounting cup 106. The actuator cap 116 is fitted onto the outwardly projecting portion of the valve stem 112 and is provided with an actuator orifice 132. The actuator orifice 132 directs the spray of the liquid product into the desired spray pattern. A dip tube 120 is attached to the lower portion of the valve body 110 to supply the liquid product to the valve assembly 104 to be dispensed. The whole valve assembly 104 is sealed to a container by the mounting gasket 108.

In operation, when the actuator cap 116 of a dispenser is depressed, the propellant forces the liquid product up the dip tube 120 and into the valve body 110 via a body orifice 122. In the valve body 110, the liquid product may be mixed with additional propellant supplied to the valve body 110 through a vapor tap 124. The vapor tap 124 helps to mix the liquid product and propellant in the valve body 110, to thereby break up the product into smaller particles suitable to be dispensed. From the valve body 110, the product is propelled through a stem orifice 126, out the valve stem 112, and through an actuator orifice 132 formed in the actuator cap 116.

One propellant used to propel liquid product from an aerosol container using the valve assembly 104 of FIG. 3 may be a B-Series propellant having a propellant pressure of 40 psig (B-40), at 70° F. (2.722 atm at 294.261 K). "Propellant pressure" refers to the approximate vapor pressure of the propellant, as opposed to "can pressure," which refers to the initial gauge pressure contained within a full aerosol container. In order to effectively dispense liquid product, the valve assembly may have a stem orifice diameter of 2×0.020" (2×0.0.508 mm), i.e., two holes of 0.020" diameter, a vapor tap diameter of 0.020" (0.508 mm), a body orifice diameter of 0.062" (1.575 mm), and a dip tube inner diameter of 0.060" (1.524 mm). One currently known aerosol air sanitizer contains hydrocarbon propellant in the amount of approximately 29.5 wt % of the contents of the dispenser assembly along with 6-8.8 wt % of glycol and pure alcohol solvent with no water present.

Hydrocarbon propellants are considered to be Volatile Organic Compounds (VOCs). The content of VOCs in aerosol air sanitizers has the potential to be regulated by federal and/or state regulatory agencies, such as the Environmental Protection Agency (EPA) and California Air Resource Board (CARB).

One way to reduce the VOC content in such aerosol air sanitizers is to reduce the content of the hydrocarbon propellant used to dispense the liquid product. However, a reduction in the propellant content can adversely affect the product performance. Specifically, reducing the propellant content in the aerosol air sanitizer may result in excessive product remaining in the container at the end of the life of the dispenser assembly (product retention) and an increase in the size of particles of the dispensed product (increased particle size). It is desirable to minimize the particle size of a dispensed product in order to maximize the dispersion of the particles in the air and to prevent the particles from "raining" or "falling out" of the air. Thus, an aerosol dispenser assembly that can satisfactorily dispense an aerosol product should include a desirable level of propellant to provide high quality product performance throughout the life of the dispenser assembly.

The "life of the dispenser assembly" is defined in terms of the pressure within the container (i.e., the can pressure), such that the life of the dispenser assembly is the period between when the pressure in the container is at its initial pressure (typically a maximum) and when the pressure within the container is substantially depleted, i.e., equal to atmospheric pressure.

The use of the terms "sanitizing" and "disinfecting" herein is consistent with Environmental Protection Agency Disinfectant Technical Science Section (DIS-TSS) nos. 01, 08, 11 and 13 (http://www.epa.gov/oppad001/sciencepolicy.htm). For example, in regard to hard surface cleaning products, DIS-TSS-01 requires a product labeled as a "disinfectant" to be tested with sixty carriers, each with three different samples (for a total of 180 samples), representing three different batches, one of which is at least 60 days old, against *Salmonella choleraesuis* (ATCC 10708—Gram negative) or *Staphylococcus aureus* (ATCC 6538—Gram positive). Under DIS-TSS-01, to support a label claim of the product being a "disinfectant," the product must provide a complete kill 59 of 60 carriers at a 95% confidence level. Thus, under DIS-TSS-01, a complete kill is essentially required for label claims of effectiveness as a "general disinfectant" or representations that the product is effective against a broad spectrum of microorganisms, including Gram-positive and Gram-negative bacteria.

In contrast to "disinfecting" and the requirements of DIS-TSS-01, which refer to a complete kill of all bacteria on a test (hard) surface, the term "sanitizing" refers to a less than complete kill of the bacteria in air. EPA regulations currently prohibit label claims of "disinfectant" on sanitizing products used in air that reduce airborne bacteria but nonetheless do not provide a complete kill of all bacteria in air. In fact, the EPA imposes separate requirements for the label use of "sanitizing" for air (DIS-TSS-11).

DIS/TSS-11 applies to products with label claims of reducing airborne microorganisms or bacteria. Glycol vapors have been shown to produce significant decreases in numbers of viable airborne bacteria within enclosed spaces. Aerosol formulations including glycols (triethylene, dipropylene, or propylene glycol) at concentrations of 5% or more will temporarily reduce numbers of airborne bacteria when adequate amounts are dispensed within a room. Unlike DIS-TSS-01, no specific standards or methods for evaluating air sanitizers have been adopted and incorporated into DIS-TSS-11.

Thus, it has been known to use certain glycols in aerosols compositions to sanitize the air in a room by decreasing the presence of airborne bacteria that are often a source of malodors. One particular glycol, triethylene glycol ("TEG"), has been found particularly effective for sanitizing air when delivered via an aerosol spray. The commercially successful OUST® air sanitizer products utilize a mixture that contains about 6 wt % of TEG. TEG has also been used as an air treatment for tobacco smoke.

There is a need for an improved aerosol composition and aerosol dispenser whereby the aerosol composition effectively controls airborne microorganisms and malodors and has a low total VOC content and whereby the aerosol dispenser delivers the composition to the ambient air with a desired particle size and spray rate to improve the air sanitization performance.

SUMMARY OF THE DISCLOSURE

This disclosure is directed to a malodor reducing and/or air sanitizing composition in combination with a spray valve, actuator and spray performance parameters to provide optimum dispersion of the composition into the air. Specifically, the aerosolized composition results in airborne particles that are sufficiently small so that the composition is distributed as a fine mist or dispersion to provide sufficient contact with malodors and/or bacteria to provide quick absorption of the malodors. The particle size of the composition is controlled through the selection of valve and actuator dimensions along with specific composition requirements including propellant contents ranging from about 10 to about 50 wt %.

The disclosed aerosol compositions comprise at least one low molecular weight polyol, i.e., a polyol having a molecular weight of about 250 or less. One particularly effective class of polyols that may be included in the disclosed aerosol composition are glycols. Preferred low molecular weight polyols are mono-, di- or tri-alkylene glycols or glycerol. A most preferred polyol is triethylene glycol (TEG) used alone or with propylene glycol.

Aqueous solutions of polyols are sometimes difficult to be effectively dispensed in aerosol form. Trigger sprays are also generally not efficient since the particle size can not be sufficiently controlled due to the homogeneity of the mixture preventing the separation of the polyol therefrom during evaporation. This disclosure provides for a two-phase oil-out emulsion in a pressurized aerosol dispenser suitable for dispensing the aqueous polyol solution as a fine mist. The particle size of this disclosure is controlled through the selection of valve and actuator dimensions as well as formulation requirements.

In one embodiment, the air treating composition according to this disclosure may comprise water, a low molecular weight (MW) polyol, an emulsifier, and a propellant as follows:

| Ingredient | Weight Percent |
|---|---|
| Water (deionized) | 20-90% |
| Low MW Polyol | 5-25% |
| Emulsifier | 0-4% |
| Propellant | 10-50% |

A co-solvent such as an alcohol may also be included in the aerosol composition to facilitate the solubilization of the ingredients. Preferably, the co-solvent is a low molecular weight monohydric $C_{1-4}$ alcohol such as ethanol, propanol, isopropanol, butanol or isobutanol. Other co-solvents, such as acetone, may also be included in the aerosol composition. In a general embodiment, an emulsifier may be present as set forth above. If the co-solvent is present in the composition in an amount that is insufficient to form an emulsion without the presence of the emulsifier, the emulsifier can be present in such instance in an amount ranging from about 0.4 to about 4 wt %. Additional adjuvants, such as fragrances, corrosion inhibitors, pH adjustors, antimicrobials, preservatives, and the like, may also be included. Preferred individual ranges for the above-listed adjuvants are from 0 to about 5 wt %, more preferably from 0 to about 2 wt %. A preferred pH of the composition is in a range of from about 8 to about 10.

The above air treating composition may be used in combination with valve and actuator dimensions and spray performance parameters as follows:

| Dimension/Property | Range |
|---|---|
| Dip Tube Inner Diameter | 0.040"-0.122" |
| Vapor Tap Diameter | 0.003"-0.020" |
| Body Orifice Diameter | 0.008"-0.062" |
| Stem Orifice | 0.014"-0.030" |
| Particle Size (initial) | ≤45 micron |
| Particle Size (200 g) | ≤45 micron |
| Spray Rate | 0.5-2.5 g/s |
| Retention | <5% |

Valve and actuator dimensions and spray performance parameters other than those above may also be present. As to the particle size, a more preferred particle size is in a range of about 25 to about 40 µm, and most preferably in a range of about 30 to about 38 µm.

The dispenser of this disclosure provides the desired small particle size and consistency throughout the life of the package. The retention rate obtained is also preferred. Procedures for determining particle size, spray rate and retention are described below.

This disclosure provides an aerosol dispenser assembly that preferably dispenses substantially all of an aqueous air treating composition (i.e., provides a low product retention) as a spray having a desirable particle size and delivery rate, while at the same time employing an optimum amount of propellant to dispense the aqueous product from the container.

In one aspect, an aerosol dispenser assembly of this disclosure comprises a container that has an aqueous air treating product and a propellant for propelling the product from the container. The propellant is preferably a hydrocarbon propellant and may be present in an amount ranging from about 10 to about 50 wt %. Preferably, the propellant is present in an amount of 45 wt % or less, even more preferably 40 wt % or less, most preferably about 35 wt % or less. The contents of the container are pressurized to from about 55 psig (3.743 atm) to about 120 psig (8.166 atm). In particular, the contents of the container are pressurized to from about 55 psig (3.743 atm) to about 80 psig (5.444 atm).

A valve attaches to the container for selectively dispensing the liquid product from the container as a mist, the mist having an average particle size of less than or equal to 45 μm (0.0018"), over at least the first 75% of the life of the dispenser assembly. Average particle size, as used herein, means mass median particle size (also known as the volumetric median) D(V,0.5) of the dispensed product, as measured by a Malvern® Mastersizer 2600 Particle Size Analyzer and as described in *Basic Principles of Particle Size Analysis*, by A. Rawle, Malvern Instruments Limited. In addition, the dispenser assembly is preferably capable of dispensing over 95 wt % of the aqueous polyol solution from the container, i.e., having less than 5 wt % product retention, more preferably 98 wt % of the aqueous air treating product from the container, i.e., having less than 2 wt % product retention.

A vapor tap is formed in the valve to facilitate thorough mixing of the propellant and the liquid product prior to dispensing, and a valve stem is disposed in the valve. The valve stem defines at least one stem orifice for flow of the combined product (i.e., the vapor from the vapor tap and liquid from the dip tube) during dispensing. The vapor tap has a diameter of about 0.003" (0.076 mm) to about 0.020" (0.508 mm), more preferably of about 0.013" (0.330 mm) to about 0.019" (0.483 mm) for dispensing in the ~20 to ~25 wt % propellant range, and of about 0.003" (0.076 mm) to about 0.013" (0.330 mm) range for dispensing in the ~15 to ~20 wt % propellant range.

A dispenser cap is mounted on the valve stem for actuating the valve to dispense the liquid product. The dispenser cap defines an exit path, through which the liquid product can be dispensed. An agitating/mixing component can be positioned in the exit path of the dispenser cap to break up or mix the liquid product in order to reduce the size of the particles before the liquid product is dispensed. The agitating/mixing component may be a spin chamber, a breakup bar, and variations thereof or other suitable component.

The valve may also have specifications as described in U.S. Pat. Nos. 6,824,079 and 7,014,127, which are commonly assigned with this application and incorporated by reference herein.

A better understanding of these and other aspects, features, and advantages of this disclosure may be obtained by reference to the accompanying drawings and detailed description, in which some preferred embodiments are illustrated and described.

BRIEF DESCRIPTION OF THE DRAWINGS

For a more complete understanding of the disclosed methods and apparatuses, reference should be made to the embodiment illustrated in greater detail on the accompanying drawings, wherein.

Figure 1:
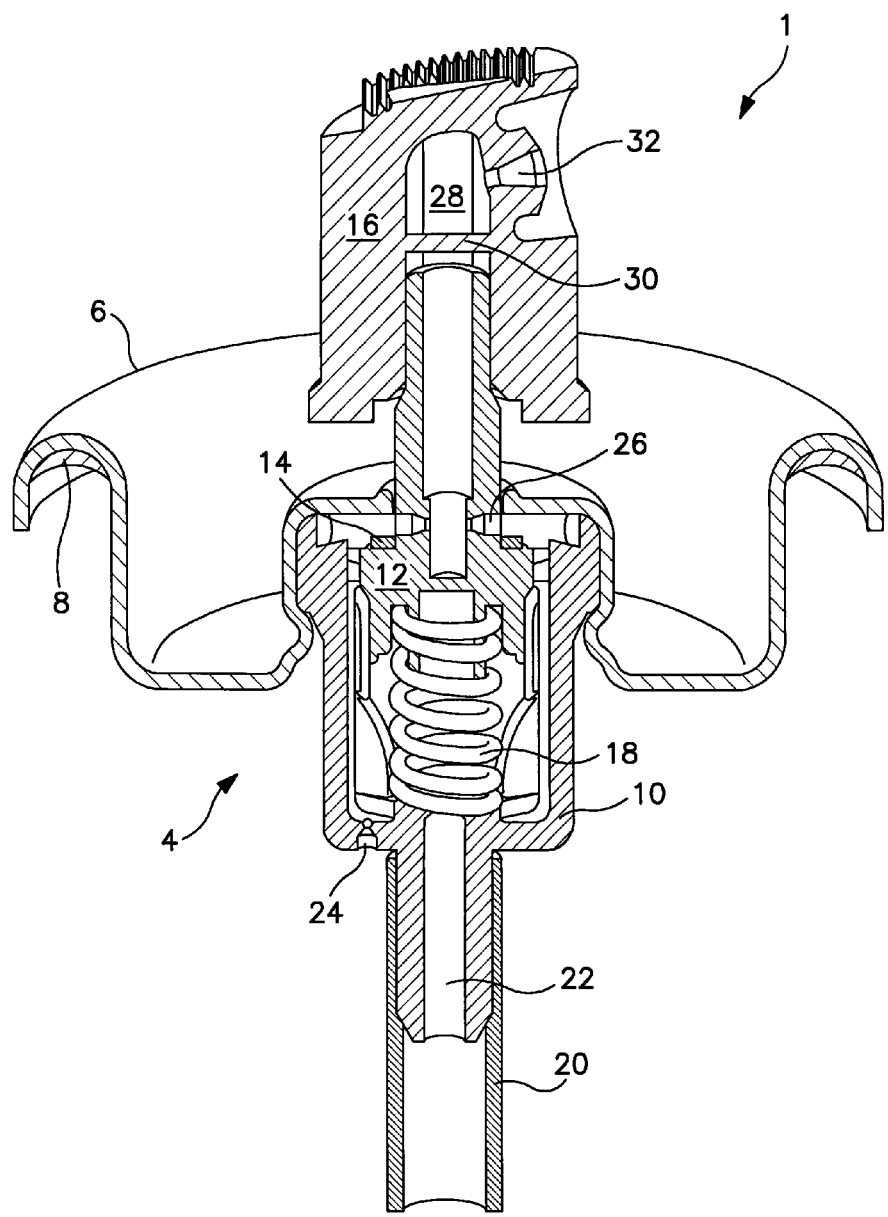
FIG. 1 is a partial cross-sectional and perspective view of a first embodiment of a valve useful in practicing the concepts of this disclosure.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

A malodor eliminating and/or air sanitizing composition in combination with a spray valve, actuator and spray performance parameters are described in greater detail below which provide optimum dispersion of the composition into the air. Preferably, the composition is delivered as an aerosol spray. The particles of the composition are sufficiently small so that the components of the composition are delivered into the ambient air as a fine dispersion to provide sufficient contact with malodors and/or airborne bacteria, and/or to provide quick absorption of the malodors. The particle size of the composition is controlled through the selection of valve and actuator dimensions along with specific composition requirements including propellant contents ranging from about 10 to about 50 wt %.

The composition according to this disclosure is directed to an aerosol air treating composition preferably comprising water, at least one low molecular weight (MW) polyol, a propellant, and optionally a solvent and/or an emulsifier.

The air treating composition of this disclosure may also comprise additional optional adjuvant such as a fragrance, a corrosion inhibitor, a pH adjusting agent, an antimicrobial agent, a preservative and mixtures thereof. One or more additional adjuvants may be present individually in amounts ranging from about 0 to about 5 wt %, more preferably from about 0 to about 2 wt %.

The components of one disclosed composition are as follows:

| Ingredient | Weight Percent |
| --- | --- |
| Water (deionized) | 20-90% |
| Low MW Polyol | 5-25% |
| Emulsifier | 0-4% |
| Propellant | 10-50% |
| Co-solvent | 0-60% |
| Fragrance | 0-5% |
| Corrosion Inhibitor | 0-2% |
| pH Adjuster | 0-2% |

Polyol

Low MW polyols suitable for use in the disclosed air treating composition preferably have a MW of about 250 grams/mole or less. One group of polyols that is particularly suitable to be included in the composition are glycols. Preferred examples of low MW polyol for use are mono- di- or tri-alkylene glycols, and glycerol. The alkylene is preferably ethylene or propylene. The most preferred low MW polyol for use is triethylene glycol (TEG). One or more low MW polyols may be used in the air treating composition, such as a low MW polyol selected from the group consisting of triethylene glycol, propylene glycol, and a mixture thereof.

The low MW polyol may be present in the composition at a concentration of from about 5 to about 25 wt % of the composition. Preferably, the composition may include from about 5 to about 20 wt % of the low MW polyol, more preferably, from about 5 to about 15 wt %, and even more preferably from about 5 to about 10 wt %. In one embodiment, the composition comprises about 6-7 wt % TEG.

Water

Compositions according to this disclosure may include a liquid carrier. Preferably, the liquid carrier comprises water, and optionally a co-solvent. Disclosed compositions may comprise from about 20 to about 90 wt % of water. In one embodiment, the composition comprises from 40-70 wt % water. However, it is noteworthy that water makes up for the weight balances of the disclosed compositions and therefore the above disclosed water content should not be considered limiting this disclosure.

Emulsifier

The air treating composition according to this disclosure may also include an emulsifier. The emulsifier may comprise one of more surfactants. There are many types of surfactants that can be included in the composition which include, but are not limited to, one more cationic surfactants, anionic surfactants, nonionic surfactants, amphoteric surfactants, and mixtures thereof.

The cationic surfactant may include a quaternary ammonium salt. Preferably, the quaternary ammonium salt has a general molecular structure of one or more alkyl groups attached to a nitrogen atom, wherein the alkyl group contains from 12 to 20 carbon atoms. Those quaternary ammonium salts may include, but are not limited to: dodecyl trimethyl ammonium bromide, tetradecyl trimethyl ammonium chloride, pentadecyl trimethyl ammonium chloride, cetyl trimethyl ammonium bromide, stearyl trimethyl ammonium bromide, stearyl trimethyl ammonium chloride, dodecyl trimethyl ammonium methyl sulphate, tallow trimethyl ammonium acetate. Other useful cationic surfactants includes: didodecyl dimethyl ammonium bromide, ditetradecyl dimethyl ammonium chloride, dipentadecyl dimethyl ammonium chloride, didodecyl diethyl ammonium chloride, ditetradecyl dipropyl ammonium chloride, ditallow diethyl ammonium chloride, didodecyl diethyl ammonium chloride, didodecyl diethyl ammonium acetate, ditallow dipropyl ammonium phosphate, and tallow dimethyl benzyl ammonium chloride.

The cationic surfactant may also include other cationic nitrogen containing compounds such as substituted immidazolium salt, substituted pyridinium salt, substituted morpholinium salt, and mixtures thereof.

The quaternary ammonium salt and other cationic nitrogen containing compounds may further comprise functional groups including, but not limited to, ether groups, ester groups, epoxy groups, amide groups, carbonyl groups, carboxylic groups, aromatic groups, amino groups, cyano group, and the like.

In the cationic surfactant, an anion, which is any anion compatible to other composition of the laundry sheet, is included in the compounds for providing electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. In some cases, the anion may also, but less preferably, carry a double charge.

The nonionic surfactant present in the air treating composition may include, but are not limited to, sorbitol esters, fatty alcohol ethoxylates, alkylphenol ethoxylates, condensates of alkanolamines with fatty acids, polyol fatty acid esters, ethoxylated polyol fatty acid esters, alkylpolyglucosides, and N-alkyl pyrrolidones. The nonionic surfactant may also include nonionic polymers, such as ethylene oxide/propylene oxide block polymers. Furthermore, additional nonionic surfactant not specifically mentioned above, may also be used. In one embodiment, the nonionic surfactant included in the air treating composition is sorbitan ester. In a refinement, the sorbitan ester may be a sorbitan monooleate.

The anionic surfactant used in this disclosure may include, but are not limited to, carboxylic acid salts, primary alkyl sulfates, alkyl ether sulfats, fatty acid sulfonates, alkyl benzene sulfonates, sulfosuccinate esters, and organic phosphate esters. Counter ions to the salts of the aforementioned anionic fabric conditioning compounds may be those of alkali metal, alkaline earth metal, ammonium, alkanolammonium, and alkylammonium types.

The amphoteric surfactant used may include, but are not limited to, tertiary amine oxide and zwitterionic quaternary ammonium compounds. The preferred amine oxides may have a general molecular structure of one or more long chain alkyl groups attached to a nitrogen atom. Such amine oxides may include, but are not limited to, didecyl amine oxide, dinonyl amine oxide, dioctyl amine oxide, didodecyl amine oxide, and the like.

Preferably, the emulsifier included in the air treating composition according to this disclosure may include a surfactant selected from a group consisting of cationic surfactants, nonionic surfactants, and mixtures thereof. In one embodiment, the cationic surfactant is a trimethyl alkyl ammonium chloride. In a refinement, the cationic surfactant is trimethyl stearyl ammonium chloride. In another embodiment, the nonionic surfactant is a sorbitan ester such as sorbitan monooleate. In yet another embodiment, the emulsifier is a mixture of trimethyl stearyl ammonium chloride and sorbitan monooleate.

Propellant

The propellant that is suitable to be included in the aerosol composition according to this disclosure may be selected from the group consisting of hydrocarbon propellants, ether propellants, CFCs, soluble or non-soluble compressed gases, and mixtures thereof. The preferred propellant according to this disclosure may include one or more hydrocarbon propellants. In one embodiment, the propellant is a mixture of propane, isobutane and n-butane. Other propellants that may be included in the disclosed aerosol composition will be apparent to those skilled in the art.

The propellant may be present in the air treating composition in a wide range of concentrations. According to one aspect of this disclosure, the composition may comprise from about 10 to about 50 wt % propellant, preferably from about 10 to about 45 wt %, more preferably from about 10 to about 35 wt %, and even more preferably from about 25 to about 35 wt %. In one embodiment, the aerosol composition comprises about 30 wt % of the propellant.

As shown in Examples C1-C4 and C7-C11 below, a wide range of propellant concentrations may be accommodated within the scope of this disclosure. Further, the inclusion of the propellant at other appropriate concentrations will be apparent to one of ordinary skill in the art.

Co-Solvent

A co-solvent may be optionally included in the aerosol composition to assist the solubilization of the ingredients therein or assist the formation of a desired emulsion. The co-solvent is preferably a low molecular weight monohydric alcohol, such as a $C_1$-$C_4$ alcohol including methanol, ethanol, propanol, isopropanol, butanol, isobutanol. Additionally, the co-solvent may also include other low molecular weight organic solvent such as acetone. In one embodiment, the co-solvent is ethanol. In another embodiment, the co-solvent is isopropanol.

As a co-solvent may contribute to the total VOC content of the composition, the presence of a co-solvent in the aerosol composition is optional and preferably in amount of no more than about 40 wt %, and preferably at a concentration lower than the water content. In a preferred embodiment, no solvent is present and, thus, an emulsifier is required to be present in an amount of from about 0.4 to about 4 wt % to insure formation of the desired emulsion. On the other hand, the emulsifier content may be reduced if a co-solvent is utilized. In one embodiment, the air treating composition does not include any emulsifier.

Fragrance

Fragrances normally consist of a mixture of a number of fragrant materials, each of which has a particular fragrant sense. The number of fragrant materials in a fragrance is typically ten or more. The range of fragrant materials may vary. The materials come from a variety of chemical classes, but in general are water-insoluble oils. In many instances, the molecular weight of a fragrance material is in excess of 150, but does not exceed 300.

Fragrance optionally included in the disclosed air treating composition may be present in an amount that is sufficient to deliver a pleasant smell that can be perceived by a consumer. In the presence of a malodor, the fragrance may be present in an amount that masks at least a substantial portion of the malodor in the air. More preferably, the fragrance is preferably present in an amount that not only completely masks airborne malodors, but also delivers a pleasant smell to be perceived by a consumer. In one embodiment, the fragrance is present in an amount ranging from about 0.01 to about 1 wt %, more preferably from about 0.01 to about 0.5 wt %, and most preferably from about 0.01 to about 0.3 wt %

The fragrance may comprise one or more fragrant materials or materials that provide chemically active vapors. In one embodiment, the fragrance can comprise and/or include volatile, fragrant compounds including, but not limited to natural botanic extracts, essences, fragrance oils, synthetic fragrant materials and so forth. As is known in the art, many essential oils and other natural plant derivatives contain large percentages of highly volatile scents. In this regard, numerous essential oils, essences, and scented concentrates are commonly available from companies in the fragrance and food businesses. Exemplary oils and extracts include, but are not limited to, those derived from the following plants: almond, amyris, anise, armoise, bergamot, cabreuva, calendula, canaga, cedar, chamomile, coconut, eucalyptus, fennel, jasmine, juniper, lavender, lemon, orange, palm, peppermint, quassia, rosemary, thyme, and so forth.

Corrosion Inhibitor

The use of water-based aerosol compositions makes possible the manufacture of products of lesser flammability and lower ingredient cost. However, the use of water in such aerosol compositions also increases the problem of corrosion on the interior of the tin-plated steel cans which are so widely used, thus leading to contamination of the aerosol product and ultimately to leaking of the can if corrosion is severe enough. For this reason, corrosion inhibitors are preferably included in water-based aerosol compositions.

If a canister susceptible to corrosion is employed with a composition containing water, one or more corrosion inhibitors may be included such as potassium phosphates, potassium nitrite, sodium phosphates, sodium nitrite, mixtures thereof, or one or more other corrosion inhibiting agents.

Di-potassium phosphate ($K_2HPO_4$) is useful as both a corrosion inhibitor and a buffer. Di-potassium phosphate may be used alone or in combination with mono-potassium phosphate ($KH_2PO_4$). Di-sodium phosphate ($Na_2HPO_4$) is also useful as both a corrosion inhibitor and a buffer and may be substituted for the di-potassium phosphate. Mono-sodium phosphate ($NaH_2PO_4$) may also be used instead of or in addition to mono-potassium phosphate. The combination of di alone or di and mono-potassium and/or sodium phosphates has been found to be enhanced by the presence of another corrosion inhibitor in the form of potassium nitrite ($KNO_2$) and/or sodium nitrite ($NaNO_2$). Accordingly, the presence of di-potassium phosphate or di-sodium phosphate may range from about 0.01 to about 1.0 wt %, more preferably from about 0.02 to about 0.25 wt %. A suitable pH range for these salts is from about 6 to about 12, more preferably from about 7 to about 11, and even more preferably from about 8 to about 10.

The amount of di-potassium phosphate or di-sodium phosphate may be reduced if a small amount of mono-potassium phosphate and/or mono-sodium phosphate is utilized as shown above in Examples 2 and 4, but the use of only di- or only mono-phosphates is possible. If used, the mono-potassium phosphate and/or mono-sodium phosphate need only be present in small amounts, but their presence may range from about 0.01 to about 1.0 wt %, more preferably around about 0.02 wt %. If utilized, the potassium nitrite can be present in amount ranging from about 0.01 to about 1.0 wt %, more preferably from about 0.07 to about 0.15 wt %. The inhibitor may also be formed in situ with potassium hydroxide and phosphoric acid or with sodium hydroxide and phosphoric acid. The mono-potassium/sodium phosphates may be added in amounts exceeding that of the di-potassium/sodium phosphates to create buffer systems ranging from acidic to alkaline pHs ranging from about 5 to about 10, preferably from about 7 to about 9.

Also, ammonium phosphates and/or ammonium nitrite may be used or combined with the corrosion inhibitors discussed above. However, ammonium nitrite is explosive and therefore presents handling problems. Tri-potassium and tri-sodium phosphates could also be used and neutralized to an acceptable pH with an acid such as phosphoric acid. Triethanolamine with sodium benzoate or with one or more the other inhibitors discussed above is a less preferred alternative for corrosion inhibition. As another alternative, corrosion inhibition may be provided by borax ($Na_2B_4O_7 \cdot H_2O$) alone or in combination with sodium nitrite or with one more of the other inhibitors discussed above.

In one embodiment, the corrosion inhibitor includes potassium monophosphate and sodium diphosphate. In a preferred embodiment, the corrosion inhibitor includes a 50/50 blend of potassium monophosphate and sodium diphosphate. Other suitable corrosion inhibitors to be included in the composition will be apparent to those of ordinary skill in the art.

pH Adjusting Agent

Suitable pH adjusting agents include conventional acids, bases, and salts thereof, such as, ammonia, alkali metal hydroxides, silicates, borates, carbonates, bicarbonates, citrates, citric acid, or mixtures thereof. In one embodiment, the pH adjusting agent is sodium hydroxide or potassium hydroxide. In another embodiment, the pH adjusting agent is ammonium hydroxide.

The pH of the composition should fall in the range of from about 6 to about 12, more preferably in the range of from about 7 to about 11, and most preferably from about 8 to about 10. The amount of pH adjusting agent included in the air treating composition to obtain the desired pH would be apparent to those of ordinary skill In the art. Preferably, the amount of pH modifying agent may be present in an amount of from about 0 to about 5 wt %, more preferably from about 0 to about 2 wt %.

Figure 2:
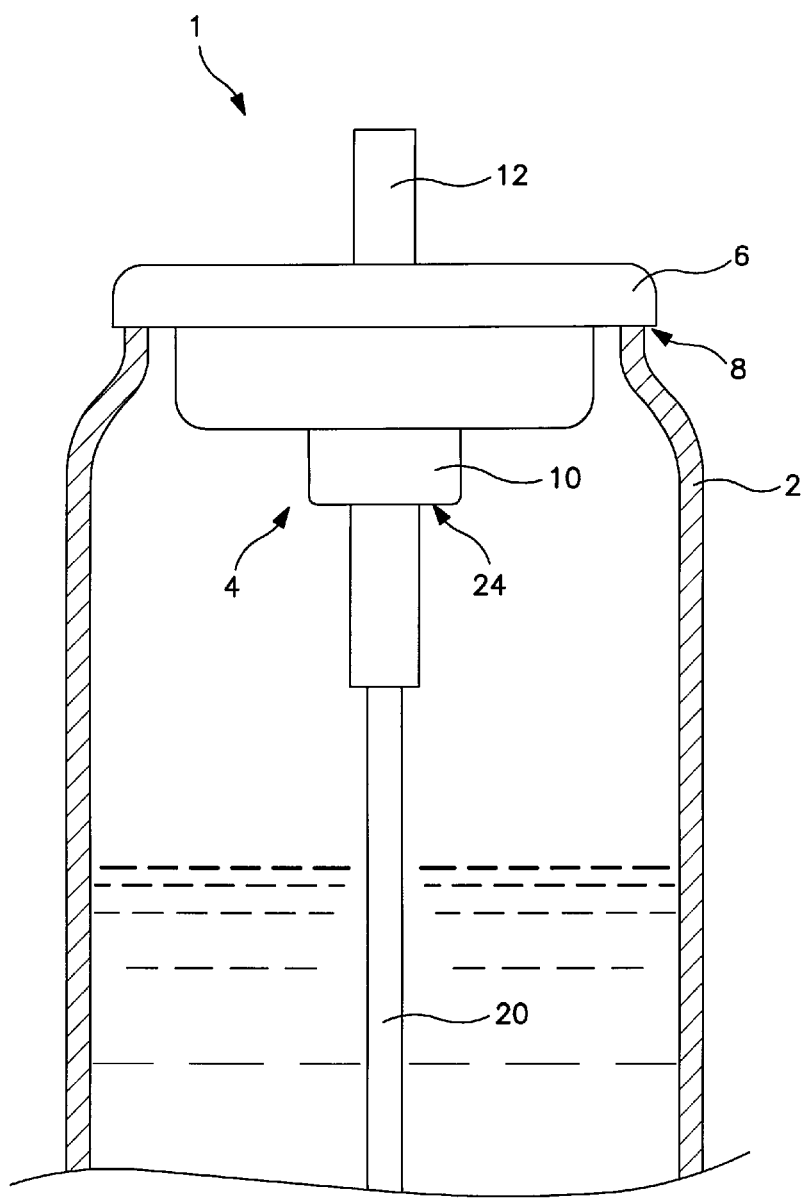
FIG. 2 is a partial front plan view of the valve of FIG. 1 as disposed within a container, also shown in part.
Figure 3:
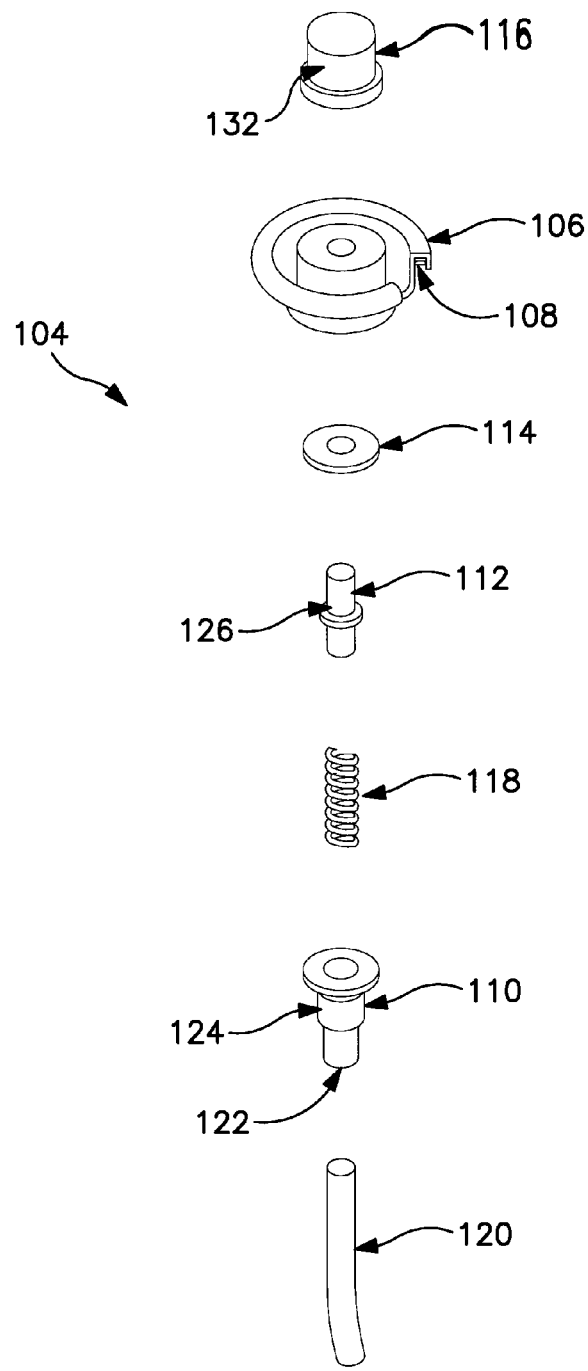
FIG. 3 is an exploded view of a conventional aerosol valve assembly and actuator cap.

As shown in FIG. 2, an aerosol dispenser assembly according to this disclosure generally comprises a container 2 with a valve assembly 4 disposed in the top thereof for selectively dispensing a liquid product from the container 2.

With reference to FIG. 1, the valve assembly 4 further comprises a mounting cup 6, a mounting gasket 8, a valve body 10, a valve stem 12, a stem gasket 14, an actuator cap 16, and a return spring 18. The actuator cap 16 defines an exit path 28 and an actuator orifice 32. The valve stem 12, stem gasket 14, and return spring 18 are disposed within the valve body 10 and are movable relative to the valve body 10. The valve body 10 affixes to the underside of the mounting cup 6, such that the valve stem 12 extends through, and projects outwardly from, the mounting cup 6. The actuator cap 16 fits onto the outwardly projecting portion of the valve stem 12, and a dip tube 20 attaches to the lower portion of the valve body 10. The whole valve assembly 4 is sealed to the container 2 by the mounting gasket 8.

While the actuator cap 16 as shown in FIG. 1 is a simple push-button actuator, it will be understood that any suitable actuator may be used, such as, for example, an actuator button with an integral overcap. In operation, when the actuator cap 16 of the dispenser 1 is depressed, it forces the valve stem 12 to move downward, opening the seal between the stem gasket and the stem orifice(s) and thereby forming a flow path from the contents of the container to the outside environment. The propellant forces the liquid product up the dip tube 20 and into the valve body 10 via body orifice 22. In the valve body 10, the liquid product is mixed with additional propellant supplied to the valve body 10 through a vapor tap 24. The vapor tap 24 helps to mix the liquid product and propellant in the valve body 10, to thereby break up the product into smaller particles suitable to be dispensed. From the valve body 10, the liquid product is propelled through at least one stem orifice 26, out the valve stem 12, and through an exit path 28 formed in the actuator cap 16.

As shown in FIG. 1, a pair of stem orifices 26 may be used. However, only one stem orifice is required. An agitating/mixing component may be provided in the exit path to further mix or agitate the product. The agitating/mixing component may be any suitable component such as, but not limited to, a spin chamber, a breakup bar, and variations thereof or other similar components. The product is then expelled from the actuator cap 16 through an actuator orifice 32, which disperses the product and produces a desired spray pattern. In one variation of the dispenser assembly, instead of a breakup bar as shown in FIG. 1, the dispenser assembly might employ a pair of breakup plates positioned in or below the exit path 28.

Several valve components are known to affect the dispensed ratio of liquid product to propellant which may include the vapor tap, the stem orifice, the body orifice, and the inner diameter of the dip tube. In general, decreasing the size of the vapor tap has the effect of creating a leaner mixture (lower propellant to liquid ratio), reducing the amount of retention, but increasing the particle size and spray rate of the dispensed product. Conversely, decreasing the size of the stem orifice, body orifice, and/or dip tube inner diameter generally decreases both the spray rate and the particle size, and potentially increases the amount of product retention.

Based on the foregoing experimentation and analysis and as discussed hereafter, certain combinations of propellant type, can pressure, and valve orifice dimensions may produce a dispenser assembly that is capable of distributing a high quality aerosol spray in the air, and thus improving the performance of the air treating composition.

Additionally, the aerosol product dispenser assembly of FIGS. 1-2 is capable of satisfactorily dispensing an aqueous, two-phase, oil-out emulsion comprising from about 10 to about 50 wt % of a propellant, and from about 5 to about 25 wt % of a water-soluble polyol with odor eliminating activity, when the diameter of the vapor tap 24 is between about 0.003" (0.076 mm) to about 0.020" (0.508 mm). More preferably, the diameter of the vapor tap 24 ranges from about 0.013" (0.330 mm) to about 0.019" (0.483 mm) when the propellant contents are in the ~20 to ~35 wt % range and the diameter the vapor tap 24 ranges from about 0.003" (0.076 mm) to about 0.013" (0.330 mm) when the propellant content is in the ~15 to ~20 wt % range. The diameter of the stem orifice 26 ranges from about 0.020" (0.508 mm) to about 0.030" (0.762 mm) when a single stem orifice is used (between about 0.014" (0.356 mm) and about 0.025" (0.635 mm) when a pair of stem orifices are used). The diameter of the body orifice 22 ranges from about 0.008" (0.203 mm) to about 0.062" (1.575 mm), more preferably from about 0.050" (1.270 mm) to about 0.062" (1.575 mm) when the propellant contents are in the ~20 to ~25% range. The diameter of the body orifice 22 ranges from about 0.008" (0.203 mm) to about 0.050" (1.270 mm) when the propellant contents are in the ~15 to ~20 wt % range and when the inner diameter of the dip tube 20 is between about 0.040" (1.016 mm) and about 0.060" (0.1.524 mm).

Thus, any of the above described valve components, propellant types, propellant pressures, and valve orifice dimensions, may be used in combination to provide a dispenser assembly according to this disclosure.

In one embodiment of this disclosure, the aerosol dispenser assembly 1 uses an A-Series propellant having a propellant pressure of about 57 psig (4.083 atm) (i.e., A-57 propellant) to dispense the liquid product from the container 2. In this embodiment, the container is initially pressurized to a can pressure of about 70 psig (4.763 atm) to about 80 psig (5.444 atm). The diameter of the vapor tap 24 in this embodiment is about 0.016" (0.406 mm). Two stem orifices 26 may be used, each having a diameter of about 0.024" (0.610 mm). The diameter of the body orifice is about 0.050" (1.270 mm), and the inner diameter of the dip tube is about 0.060" (1.524 mm).

Another embodiment of the dispenser assembly 1 employs a single stem orifice 26. In this embodiment, the dispenser assembly 1 also uses the A-57 propellant and a can pressure of about 70 psig (4.763 atm) to about 80 psig (5.444 atm) to dispense the liquid product from the container 2. The diameter of the vapor tap is about 0.016" (0.406 mm), the diameter of the single stem orifice is about 0.025" (0.635 mm), the diameter of the body orifice is about 0.062" (1.575 mm), and the inner diameter of the dip tube is about 0.060" (1.524 mm).

These embodiments of the dispenser assembly are capable of dispensing the liquid product contained within the container as a mist having an average particle size of less than or equal to 45 μm (0.0018"), over at least 75% of the life of the dispenser assembly. Because the dispensed mist has such a small particle size, the particles are more easily dispersed in the air and less fallout is experienced than with higher particle size producing assemblies containing limited propellant amounts of from about 10 to about 50 wt %. This reduction in the amount of fallout increases the dispenser assembly's odor eliminating (removal) efficacy and helps to prevent undesirable residue of the liquid product from settling on flat surfaces, such as, countertops, tables, or floors. Additionally, the spray rate is preferably in a range from about 0.5 g/s to about 2.5 g/s for at least 75% of the life of the dispensing assembly.

While the preferred particle size and spray rate is described above and hereafter in test examples, particle size and spray rate can vary from dispenser to dispenser and due to various conditional variations such as, but not limited to, temperature, humidity and/or the like.

The spray rate of 200 g/s and particle size of 200 D(V,0.5) are late in life product performance measurements preferably collected at about 50-75% of the life of the product. Because the spray rate and particle size measurements consume product in their determination, the process of collecting two spray rate and two particle size measurements results in a decrease in product weight, which depends upon the spray rate. Therefore, the value for the product weight is held constant at about 45% of the initial product weight. This choice of initial product weight before late in life measurement allows the measurement to be suitably collected for a 260 gram fill weight in an 80 gram package for spray rates up to 2.5 g/s, without running out of dispensable product in the process.

Moreover, these preferred embodiments of the dispenser assembly are capable of dispensing over 95 wt % of the liquid product from the container, i.e., leaving less than 5 wt % product retention, and more preferably 98 wt % of the liquid product from the container, i.e., having less than 2 wt % product retention. In one embodiment, substantially all of the product may be dispensed in the air. Also, by minimizing the amount of product retained in the container at the end of the life of the dispenser assembly, less liquid product is wasted. This is important from a consumer satisfaction standpoint, since consumers tend to be more satisfied with a dispenser assembly when substantially all of the product is dispensed.

Additional embodiments of the composition, valve, actuator overcap and spray performance parameters are described in the following examples. The examples are meant to be illustrative and not to be limiting.

The comparative example C7 is a single-phase system. No shaking is required and no two-phase emulsion is present.

All of the examples C1-C4 and C7-C11 have a propellant level of no more than about 50 wt %. However, higher propellant values, such as 55 wt %, 60 wt %, 65 wt %, 70 wt %, 75 wt % or even 80 wt % may also be suitable and are considered to be within the scope of this disclosure. The incorporation of the propellant at various other concentrations will be apparent to those skilled in the art.

Ethanol content in examples C1, C2, C3, and C4 has a maximum level of 38.4 wt %. In the comparative example C7, the contents of the composition dissolve in one another and form a single phase product. Without being bound by any particular theory, the presence of solvent (ethanol) may contribute to the formation of the single phase liquid. However, ethanol increases the total VOC content and, depending on the amount of ethanol present, can result in a composition having a high VOC content, such as shown for example by composition C7 which contains ethanol and no water. In order to reduce the total VOC content of the composition, a portion or all of the ethanol content of the composition may be replaced with water, such as shown for example by compositions C1-C4 and C8-C11. Since water is not classified as a VOC, the total VOC content of the product is reduced when water is present. In some examples (not shown) the ethanol content is sufficient to completely dissolve the added water. In example C3 and C4, however, the water content is comparable to the ethanol content and therefore a two-phase system is formed. The hydroalcoholic mixture forms a two-phase oil-out emulsion when shaken, the stability of the so-formed emulsion may be enhanced by the presence of the emulsifier (in example C3).

Example C8-C11 shows the inclusion of a propellant in an amount of about 30 wt % or higher. However, compared to the comparative example C7 discussed above, the total VOC contents of the compositions C8-C11 are significantly

EXAMPLES

Compositions

| | Composition | | | | | | | | |
|---|---|---|---|---|---|---|---|---|---|
| | C1 | C2 | C3 | C4 | C7 | C8 | C9 | C10 | C11 |
| Water | 72.5% | 67.4% | 34.1% | 34.8% | 0% | 62.3% | 57.3% | 45.5% | 20% |
| Co-solvent | 0% | 0% | 34.5% | 38.4% | 63.9% | 0% | 0% | 5.0% | 2.0% |
| Low MW Polyol | 6.1% | 6.1% | 6.1% | 6.1% | 6.1% | 6.2% | 6.2% | 5% | 25% |
| Emulsifier | 1.4% | 0.81% | 0.61% | 0% | 0 | 0.86% | 0.83% | 4.0% | 2.0% |
| Fragrance | 0.15% | 0.15% | 0.15% | 0.15% | 0.15% | 0.15% | 0.15% | 0.5% | 0.25 |
| Corrosion Inhibitor | 0% | 0.35% | 0.07% | 0.32%* | 0% | 0.41% | 0.40% | 0.50% | 0.75% |
| pH Adjustor | 0% | 0.39% | 0.05% | 0% | 0% | 0.08% | 0.10% | 0.50% | 0% |
| Surface Disinfectant | 0% | 0% | 0% | 0.2%** | 0% | 0% | 0% | 0% | 0% |
| Propellant | 20.0% | 24.96% | 24.57% | 20.0% | 30.0% | 30% | 35% | 40% | 50% |
| Total VOC Content | 20% | 25.0% | 59.1% | 58.4% | 93.9% | 30% | 30% | 45% | 52.0% |

*Blend of $KNO_2$(0.12%) + $K_2HPO_4$(0.02%) + $KH_2PO_4$(0.18%)
**Onyxide 3300, or alkyl dimethylbenzylammonium saccharinate Examples C1, C2, C3, and C4 form oil-out emulsions when shaken. Formation of an oil-out emulsion is critical to maintaining good spray performance.

All of the examples C1-C4 and the comparative example C7 have a pH value of from about 8.5 to about 9.5 for the liquid carrier including the aqueous and the optional alcoholic portions.

decrease by the reduction of the content of the co-solvent. Preferably, the aerosol composition may have a total VOC content of no more than 60 wt %.

The following two tables summarize suitable valves and overcaps, which when used with the respective formulas set forth above, produce the spray performance parameters reported in the third following table.

Valve

| | Label/Example | | | | | | |
|---|---|---|---|---|---|---|---|
| | V1 | V2/V3 | V4 | V5/V6 | V7 | V8 | V9 |
| Vapor Tap | 0.005" | 0.016" | 0.016" | 0.013" | 0.020" | 0.020" | 0.020" |
| Body Orifice | 0.013" | 0.050" | 0.050" | 0.050" | 0.050" | 0.050" | 0.050" |
| Dip Tube Inner Diameter | 0.060" | 0.060" | 0.050" | 0.050" | 0.060" | 0.120" | 0.120" |
| Stem Orifice | 4 × 0.024" | 2 × 0.024" | 2 × 0.020" | 2 × 0.020" | 2 × 0.020" | 1 × 0.020" | 1 × 0.020" |
| Supplier | Precision Valve Corp. | Precision Valve Corp. | Precision Valve Corp. | Precision Valve Company | Precision Valve Company | Precision Valve Company | Precision Valve Company |

Actuator Overcap

| | Label/Example | | | | | | |
|---|---|---|---|---|---|---|---|
| | AO1 | AO2/AO3 | AO4 | AO5/AO6 | AO7 | AO8 | AO9 |
| Form | 2 Piece Mechanical Breakup Button | Actuator Overcap | 2 Piece Mechanical Breakup Button | 2 Piece Mechanical Breakup Button | Actuator Overcap | Actuator Overcap | 2 Piece Mechanical Breakup Button |
| Stem Tortuosity | Bent w/ Breakup Geometry | Straight Tubular | Bent w/ Breakup Geometry | Bent w/ Breakup Geometry | Straight Tubular | Straight Tubular | Bent w/ Breakup Geometry |
| Spin Chamber | Yes | No | Yes | Yes | No | No | No |
| Breakup Bar | No | Yes | No | No | No | No | Yes |
| Exit Orifice Diameter | 0.018" | 0.021" | 0.016" | 0.020" | 0.021" | 0.021" | 0.021" |

Spray Performance Parameters

| | Label/Example | | | | | | | |
|---|---|---|---|---|---|---|---|---|
| | SP1 | SP2 | SP3 | SP4 | SP5/SP6 | SP7 | SP8 | SP9 |
| Container Volume/ml | 359.5 | 359.5 | 359.5 | 554.7 | 359.5 | 472.7 | 474 | 474 |
| Fill Weight/g | 259.7 | 259.7 | 259.7 | 346.6 | 259.7 | 296.7 | 300 | 300 |
| Initial Spray Rate/g/s | 0.61 | 1.35 | 1.34 | 0.82 | 1.01 | 1.20 | 0.51 | 1.02 |
| Initial Particle Size D(V, 0.5)/micron | 41 | 37 | 40 | 39 | 58 | 33 | 35 | 35 |
| Spray Rate 200/g/s | 0.62 | 1.17 | 1.20 | 0.67 | 0.90 | 0.86 | 0.35 | 0.72 |
| Particle Size 200 D(V, 0.5)/micron | 43 | 38 | 42 | 31 | 61 | 41 | 39 | 37 |
| Retention/% | 2 | <2 | <2 | <2 | <2 | <2 | <2 | <2 |

The valve and actuator overcap combination for standard package revealed in V1 and A01 can alternatively be used for Examples C1 and C2 with similar performance results. Valve V7 for composition C7 is also available from Summit Packaging Systems (with body orifice=0.062", stem orifice=1.times.0.025", dip tube ID=0.060", and vapor tap=0.020").

In one embodiment, the aerosol dispenser assembly may comprise a container containing an odor eliminating composition for treating air and a valve attached to the container for selectively dispensing the composition, wherein the dispensed composition has a mass median particle size of less than or equal to 45 µm over at least 75% of a life of the dispenser assembly and a spray rate in a range from about 0.5 g/s to about 2.5 g/s over at least 75% of the life of said dispenser assembly; and wherein the valve includes a vapor tap with a diameter in a range from about 0.003" to about 0.20", and a valve stem defining at least one stem orifice, a sum of diameters of the at least one stem orifice being at least 0.010".

The air treating composition may provide one or more of the following advantages: (1) odor elimination; (2) fine mist; (3) adequate spray rate; (4) low retention; (5) lack of can corrosion; (6) low manufacturing cost; and (7) absence of toxicity or other deleterious effects.

The above examples were tested using predetermined test procedures. The following is an overview of the conditions and parameters of the test procedures used to measure conditions and results, including spray rate, particle size and retention.

Spray performance was evaluated at ambient indoor conditions, i.e. 70° F. and ordinary humidity. Samples were stored at ambient indoor conditions for at least 24 hours before tests.

Spray rates were determined through weight change during a 10 second spray, are reported as grams per second, and are averaged over two sprays during the first 40 seconds of sample life. The actuator is completely depressed during the measurement. The can is shaken appropriately before spraying, allowing up to 2-4 seconds between shaking and spraying.

Spray rate 200 were collected after spraying the sample down to 200 g (formula+package) and are averaged over two measurements.

Particle size is mass median diameter, D(V,0.5)(μm) reported using a Malvern® laser diffraction particle size analyzer equipped with a 300 mm lens. Aerosols were sprayed with the spray tip 18" from the probe beam. A cutoff was applied at 301.7 μm to eliminate ghost peaks caused by "beam steering." Spray times for particle size measurements were between 5 and 10 seconds, depending on the obscuration of the spray. Results were averaged over two measurements collected during the first 40 seconds of sample life. Samples were appropriately shaken before measurements were taken, allowing up to 2-4 seconds between shaking and spraying.

Particle size 200 is D(V,0.5) was also determined using a Malvern® analyzer, and was collected on samples that were sprayed down to 200 grams (formula+package) and averaged over at least two measurements. Aerosols were sprayed with the spray tip 18" from the probe beam. Typically, particle size 200 and spray rate 200 measurements were alternated until two of each were completed.

Spray-down was accomplished by spraying cans for 10 second intervals once per hour, usually for a maximum of 6 sprays per day. This process tended to deplete the can pressure, which was regained on standing for 24 hours or so, depending on the amount of spray-down. Other critical measurements, such as particle size and spray rate were not measured within 24 hours of substantial spray down (3 or more ten second sprays).

Product retention is the weight of material remaining in the aerosol after complete discharge of the propellant through the spray-down procedure. The weight of retained product was determined by the difference in the final weight of the fully discharged package (when internal pressure equals ambient pressure) minus the weight of the package following opening the container and rinsing the remaining contents away with acetone (and drying). Product retention may be reported as grams retained or percent retained.

While only certain embodiments have been set forth, alternatives and modifications will be apparent from the above description to those skilled in the art. These and other alternatives are considered equivalents and within the spirit and scope of this disclosure and the appended claims.

What is claimed:

1. An aerosol article for treating air comprising:
   (1) a dispensing container including a spray head and (2) a composition for dispensing from said container, wherein said composition based on 100 wt. %, comprises
   5 wt. % to about 25 wt. % of at least one polyol having a molecular weight of about 250 grams/mole or less;
   from about 0.4 wt. % to about 4 wt. % emulsifier;
   from about 10 wt. % to about 50 wt. % propellant;
   from about 20 wt. % to about 90 wt. % water;
   from 0 wt. % to about 60 wt. % co-solvent which is one or more of a low molecular weight monohydric alcohol or acetone; and
   optionally, one or more components selected from the group consisting of fragrances, corrosion inhibitors, pH adjustors, antimicrobials, and preservatives;
   wherein when said co-solvent is present in said composition in an amount sufficient to form an emulsion in absence of said emulsifier, said emulsifier can then be present in an amount of from 0 to about 4 wt. %; and
   wherein said composition is a two-phase oil-out emulsion and said spray head is adapted so that upon said composition being dispensed from said spray head of said dispensing container, said composition has an average particle size of less than or equal to 45 μm over at least 75% of a life of said composition and a spray rate in a range from about 0.5 g/sec to about 2.5 g/sec over at least 75% of said life of said composition.

2. The aerosol article for treating air according to claim 1, wherein the propellant is present in an amount of about 10 to about 35 wt. %.

3. The aerosol article for treating air according to claim 1, wherein said emulsifier is a combination of sorbitan monooleate and a quaternary ammonium salt.

4. The aerosol article for treating air according to claim 1, wherein a corrosion inhibitor is present and said corrosion inhibitor is potassium phosphate, sodium phosphate, potassium nitrite, sodium nitrite or mixtures thereof.

5. The aerosol article for treating air according to claim 1, wherein the polyol is one or more of a monoalkylene glycol, dialkylene glycol, trialkylene glycol or glycerol.

6. The aerosol article for treating air according to claim 1, wherein the composition has a pH in a range of about 8 to about 10.

* * * * *